(12) United States Patent
Kute et al.

(10) Patent No.: US 7,731,650 B2
(45) Date of Patent: Jun. 8, 2010

(54) MAGNETIC CAPTURE AND PLACEMENT FOR CARDIAC ASSIST DEVICE

(75) Inventors: Stephanie Kute, Stewartsville, NJ (US); Steven Zung-Hong Wu, Santa Rosa, CA (US)

(73) Assignee: Ethicon, Inc., Somerville, NJ (US)

( * ) Notice: Subject to any disclaimer, the term of this patent is extended or adjusted under 35 U.S.C. 154(b) by 1743 days.

(21) Appl. No.: 10/881,510

(22) Filed: Jun. 30, 2004

(65) Prior Publication Data
US 2006/0004248 A1  Jan. 5, 2006

(51) Int. Cl.
*A61F 2/00* (2006.01)
(52) U.S. Cl. ...................................................... 600/37
(58) Field of Classification Search .................. 600/37, 600/16–18, 29–32; 128/897–899, DIG. 25
See application file for complete search history.

(56) References Cited

U.S. PATENT DOCUMENTS

| | | | |
|---|---|---|---|
| 5,702,343 A | 12/1997 | Alferness | |
| 5,843,025 A * | 12/1998 | Shaari | 602/53 |
| 6,076,013 A | 6/2000 | Brennan et al. | |
| 6,425,856 B1 | 7/2002 | Shapland et al. | |
| 6,595,912 B2 | 7/2003 | Lau et al. | |
| 6,682,476 B2 | 1/2004 | Alferness et al. | |
| 6,702,732 B1 | 3/2004 | Lau et al. | |
| 6,723,038 B1 | 4/2004 | Schroeder et al. | |
| 6,746,471 B2 | 6/2004 | Mortier et al. | |
| 2002/0056461 A1 | 5/2002 | Jayaraman | |
| 2003/0078465 A1 | 4/2003 | Pai et al. | |
| 2004/0111101 A1 | 6/2004 | Chin | |

\* cited by examiner

*Primary Examiner*—Samuel G Gilbert

(57) ABSTRACT

A system and method for capturing and placing a cardiac assist device on a heart. A cardiac assist device is delivered to a chest cavity of a being through an opening provided in a chest wall. A magnetically charged tether is provided at each corner or extremity of the cardiac assist device. Capture instruments magnetically couple with a corresponding tether. The magnetically coupled instruments and tethers then maneuver the cardiac assist device to a desired position about the heart. The cardiac assist device is then secured directly to the heart or to anchoring devices separately provided and secured to the heart.

55 Claims, 14 Drawing Sheets

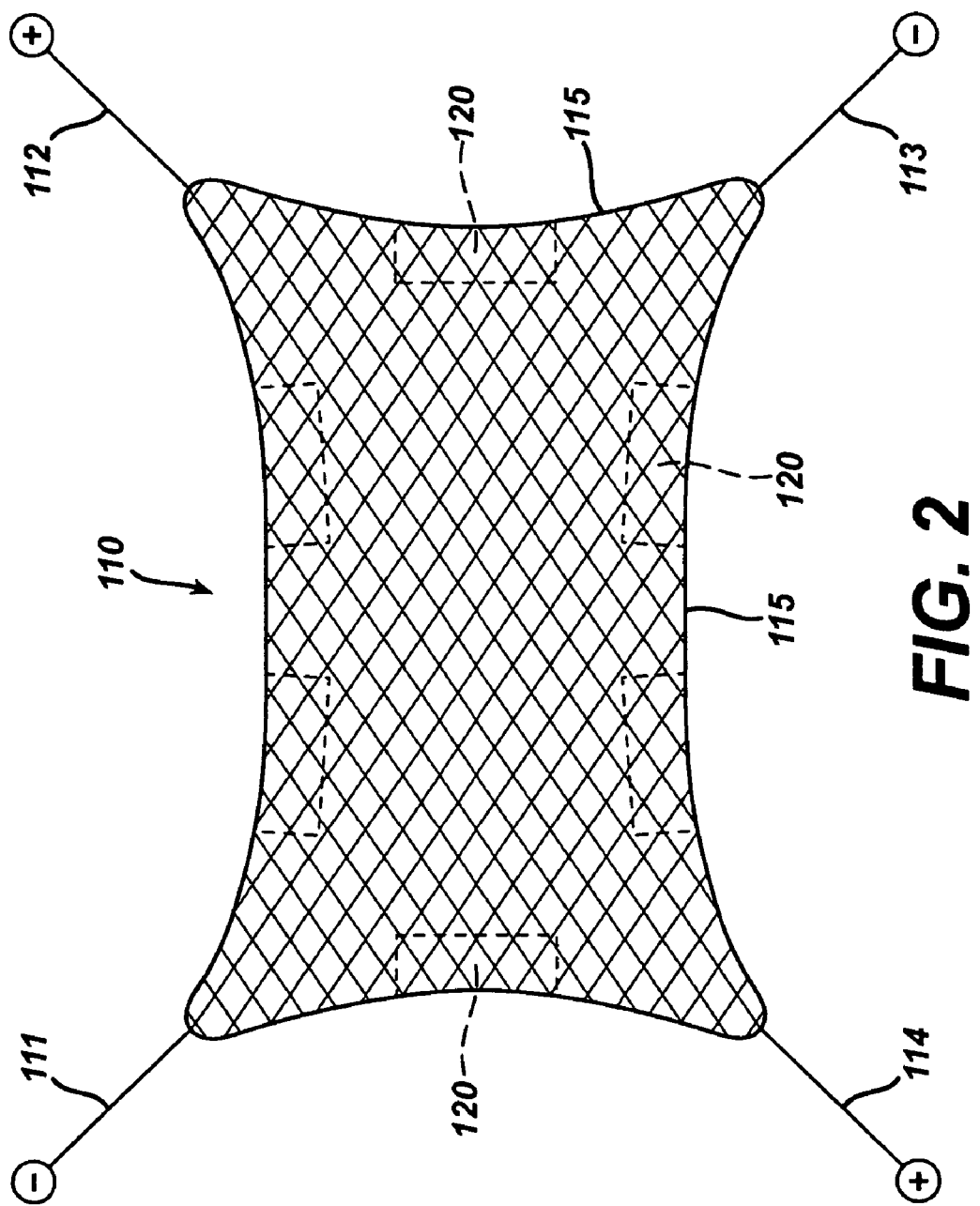

MAGNETIC CAPTURE AND PLACEMENT FOR CARDIAC ASSIST DEVICE

BACKGROUND OF THE INVENTION

1. Field of the Invention

This invention relates to systems and methods for capturing and placing a cardiac assist device. More specifically, this invention relates to systems and methods for magnetically capturing, placing and securing a chronic heart failure passive restraint device around desired portions of a heart.

2. Prior Art

Heart failure syndrome is a highly debilitating and degenerative disorder resulting from damage to the heart muscle. The damage to the heart muscle may be caused by a number of conditions, including coronary artery disease, long standing hypertension, leaky heart valve(s), and infections.

Heart failure typically occurs when a weakened heart cannot pump an adequate amount of blood to meet the demands of the body's other organs and tissues. The defining characteristic in the progression of heart failure is that there is eventually a reduction of the heart's ability to meet the metabolic needs of the body.

Whatever the cause or source of damage, the heart's ability to pump adequate amounts of blood to support the body's needs is diminished, and the progressive deterioration of cardiac physiology and function begins. The inadequate supply of oxygen-rich blood often causes people with heart failure to experience shortness of breath and fatigue during even routine daily activities. As the condition progresses, the contraction rate of the heart increases in response to decreasing cardiac output. As a result, the chambers of the heart, particularly the ventricles of the heart, become increasingly enlarged as the heart tries to compensate for the inefficiencies. FIGS. 1a-1c show representative stages of progressive deterioration of a heart, wherein FIG. 1a shows a normal heart H with appropriately sized atrial chambers 1 and 2, and appropriately sized ventricular chambers 3 and 4, FIG. 1b shows slightly enlarged ventricular chambers 3 and 4, and FIG. 1c shows increasingly enlarged ventricular chambers 3 and 4. Ultimately, a complex process of damaging structural and functional changes to the heart results. Ventricular dilation results in thinning of the ventricular wall, which elevates the wall stress. This increase in wall stress leads to altered gene expression at the cellular level that results in attenuated adrenergic response, impaired myocyte function, cardiomyocyte hypertrophy, altered extracellular matrix production and cell death. This remodeling process continues as the body tries to continually compensate for ineffective pumping and eventually leads to heart failure.

The disease of heart failure is common, lethal, and expensive to treat. An estimated 5.1 million Americans have heart failure with approximately 500,000 new cases diagnosed each year. In 1999, an estimated $20.3 billion in directs costs were spent for the care of heart failure patients. Heart failure is also the most common cause of hospitalization for patients 65 years and older in the United States. The mortality rate is 50% at five years for patients diagnosed with heart failure, and to date, there are limited treatment alternatives available.

Certain cardiac disease treatment devices have been proposed to help alleviate the disease of heart failure. For example, U.S. Pat. No. 6,425,856 provides a cardiac constraint device comprised of a jacket made of biologically compatible material. The jacket is configured to surround a valvular annulus of the heart and at least the ventricular lower extremities of the heart. FIG. 1d illustrates how the jacket 20 may be positioned around the heart 10 to improve cardiac function. The jacket works on a passive, mechanical level to reduce periodic myocardial over-stretch and wall stress, and serves as a constant "reminder" to the heart of how it should perform. The jacket thus encourages down-regulation of increased local neurohormonal activity, and reduction or elimination of cardiomyocyte maladaptive gene expression. These actions may halt the progressive deterioration of the heart and may stimulate reverse remodeling of the heart. Once positioned as desired around the heart, the jacket 20 is sutured to the heart. Ideal positioning of the jacket around the heart has proved problematic, however, particularly where endoscopic tools and techniques are used.

An alternative procedure for surrounding a heart with a cardiac assist device proposes placing a rectangular sheet of mesh underneath the heart and then pulling corners of the mesh sheet up and around the heart. Each corner of the mesh sheet is provided with suture tethers that are pulled in a designated sequence in order to wrap the mesh sheet around the heart. The instruments used to grab the tethers of the mesh sheet are placed through different ports in the chest wall. Capturing and pulling the tethers securely in the desired sequence is time consuming however and prone to errors as the instruments used have limited maneuverability, and the tethers frequently pull free from the capturing instruments.

Therefore, a need exists for systems and methods that provide more reliable capture and placement of a cardiac implant or cardiac assist device about a heart.

SUMMARY OF THE INVENTION

Accordingly, a system for the capture and placement of a cardiac assist device is provided. The system for the capture and placement of a cardiac assist device comprises a cardiac assist device inserted into a chest cavity of a body. The cardiac assist device further comprises a wrap made of a flexible bio-compatible material for enveloping at least a portion of the heart, the wrap serving as the cardiac assist device. In some embodiments of the invention the wrap is a rectangular or square shaped mesh sheet. In other embodiments of the invention, the wrap is a triangular or tri-laterally shaped sheet. The cardiac assist device further comprises at least one tether, each tether extending from a corner or extremity of the cardiac assist device and having a magnetic charge.

The systems of the invention further comprise at least one instrument that magnetically couples with one of the at least one tether, each instrument being independently inserted into a chest cavity of a being and having a magnetic charge, the magnetic charge of each instrument corresponding to an oppositely charged one of the at least one tether, wherein each magnetically coupled instrument and tether are maneuverable by a medical professional via proximal portions of each instrument extending externally from the chest cavity, each magnetically coupled instrument and tether being maneuvered to place the cardiac assist device at a desired position on the heart. Color coding of the tethers and instruments may be used in addition to magnetic coupling in order to help identify which tether corresponds to which instrument and/or to help identify the sequence in which the coupled instruments and tethers are to be maneuvered in order to position the cardiac assist device wrap as desired about the heart.

Ports provided through the chest wall of a patient permit insertion of the various capture instruments and visualizing means. The visualizing means may be an endoscope, a fiberoptic cable or a camera on an elongate member, for example. One of the ports also provides the access means for inserting into the chest cavity a delivery tube containing the cardiac assist device. Magnetically charged tethers protruding from an open end of the delivery tube are coupled with a corresponding capture instrument. Proximal portions of the magnetically coupled tethers and instruments extend externally from the chest cavity and are manipulated by a medical professional to withdraw the cardiac assist device from the delivery tube. The withdrawn cardiac assist device is then placed under the heart for eventual wrapping in a desired position about the heart. The magnetically coupled capture instruments and corresponding tethers perform the desired manipulations with visual assistance from the endoscopic or other visualization means.

The system for capturing and placing a cardiac assist device further comprises devices and techniques for securing or attaching the cardiac assist device in place once the desired position is achieved. The securing devices and techniques may include sutures, ties, clips, or adhesives that secure the device directly to the heart, or other anchoring devices placed directly on the heart to which the cardiac assist device is then attached. The cardiac assist device may be magnetically or non-magnetically secured to the anchoring devices. The anchoring devices are also each secured to the surface of the heart using sutures, clips, staples, adhesives or other known securing means. Securing the cardiac assist device to the anchoring devices may be performed endoscopically as well, using the same ports once occupied by the capture instruments or other equipment during the procedures according to the invention.

Further, a method is provided for the capture and placement of a cardiac assist device. The method for the capture and placement of a cardiac assist device at least comprises providing at least three ports providing access to a chest cavity through a chest wall of a patient; placing a visualization means into the chest cavity through one of the at least three ports; placing a cardiac assist device having at least one tether into a delivery tube, each tether having a magnetic charge; inserting the delivery tube into a chest cavity of the patient through one of the at least three ports; separately inserting at least one instrument into the chest cavity through at least one of the at least three ports, each instrument having a magnetic charge opposite the magnetic charge of a corresponding one of the at least one tether; magnetically coupling each instrument with a corresponding tether to withdraw the cardiac assist device from the delivery tube and to maneuver the cardiac assist device to a desired position over the heart; removing the delivery tube from the chest cavity and port; securing the cardiac assist device to the heart in the desired position; and removing the instruments from the chest cavity and being. The method may further comprise securing the cardiac assist device to anchoring devices separately placed onto a surface of the heart.

In some embodiments of the invention, the endoscope or other visualization means is temporarily inserted into the chest cavity through one of the ports in which one of the capture instruments is also inserted into the chest cavity. The endoscope or other visualization means is initially positioned to view the insertion of the delivery tube and the withdrawal of the cardiac assist device therefrom. After removal of the delivery tube from its port, the endoscope or other visualization means may be transferred to the port previously occupied by the delivery tube. In this manner, the endoscope or other visualization means is positioned to view the manipulations of the capture instruments and tethers according to the invention.

In other embodiments of the invention, the endoscope or other visualization means is inserted into the chest cavity through an additional, optional port, wholly independent of the capture instruments and delivery tube. In this case, the endoscope or other visualization means need not be transferred from one port to another during the procedure. Regardless of the port the endoscope or other visualization means is inserted through, the endoscope or other visualization means permits the medical professional to view the cardiac assist device and various instruments, tethers, anchoring devices and procedures involved in the systems and methods of the invention in an unobtrusive manner.

The system and methods of the invention provide several advantages and solve many of the problems posed by prior known devices and methods of capture and placing a cardiac assist device. The magnetic attachments provided in the capture instruments and tethers of the present invention are reliably secured to one another and more readily pull portions of the cardiac assist device in an appropriate sequence to fit the cardiac assist device to the heart as desired. The endoscopic nature of the methods of the invention also renders the systems of the invention easier to manipulate to more readily fit the cardiac assist device to the contours of the heart. Further, once positioned as desired, the cardiac assist device may also be secured to the heart, or attached to anchoring devices secured to the heart, using similar endoscopic techniques. Further, the magnetic components of the invention are relatively simple and inexpensive to manufacture and can be easily used with anchoring devices, when provided, on the heart. Thus, the present invention simplifies endoscopic procedures for placing and securing a tethered cardiac assist device about the heart.

The above and other features of the invention, including various novel details of construction and combinations of parts, will now be more particularly described with reference to the accompanying drawings and claims. It will be understood that the various exemplary embodiments of the invention described herein are shown by way of illustration only and not as a limitation thereof. The principles and features of this invention may be employed in various and numerous embodiments without departing from the scope of the invention.

BRIEF DESCRIPTION OF THE DRAWINGS

These and other features, aspects, and advantages of the apparatus and methods of the present invention will become better understood with regard to the following description, appended claims, and accompanying drawings where:

FIG. 2 illustrates a generally rectangular-shaped cardiac assist device wrap according to the invention.

DETAILED DESCRIPTION OF THE INVENTION

Figure 1A:
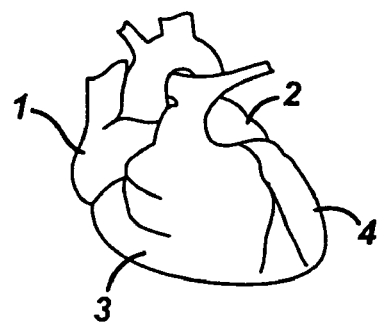
FIGS. 1a-1c illustrate progressive states of deterioration of a heart representative of heart failure conditions.
Figure 1B:
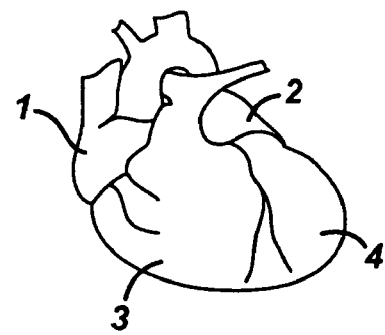
Figure 1C:
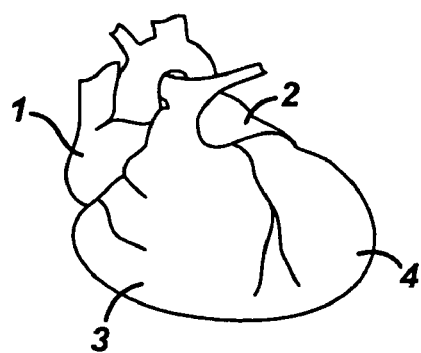
Figure 1D:
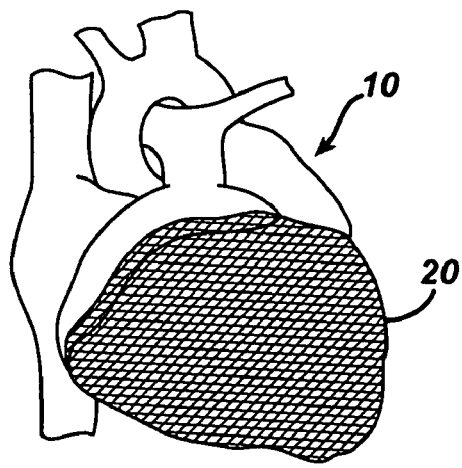
FIG. 1d illustrates a prior art mesh jacket placed around a heart.
Figure 3:
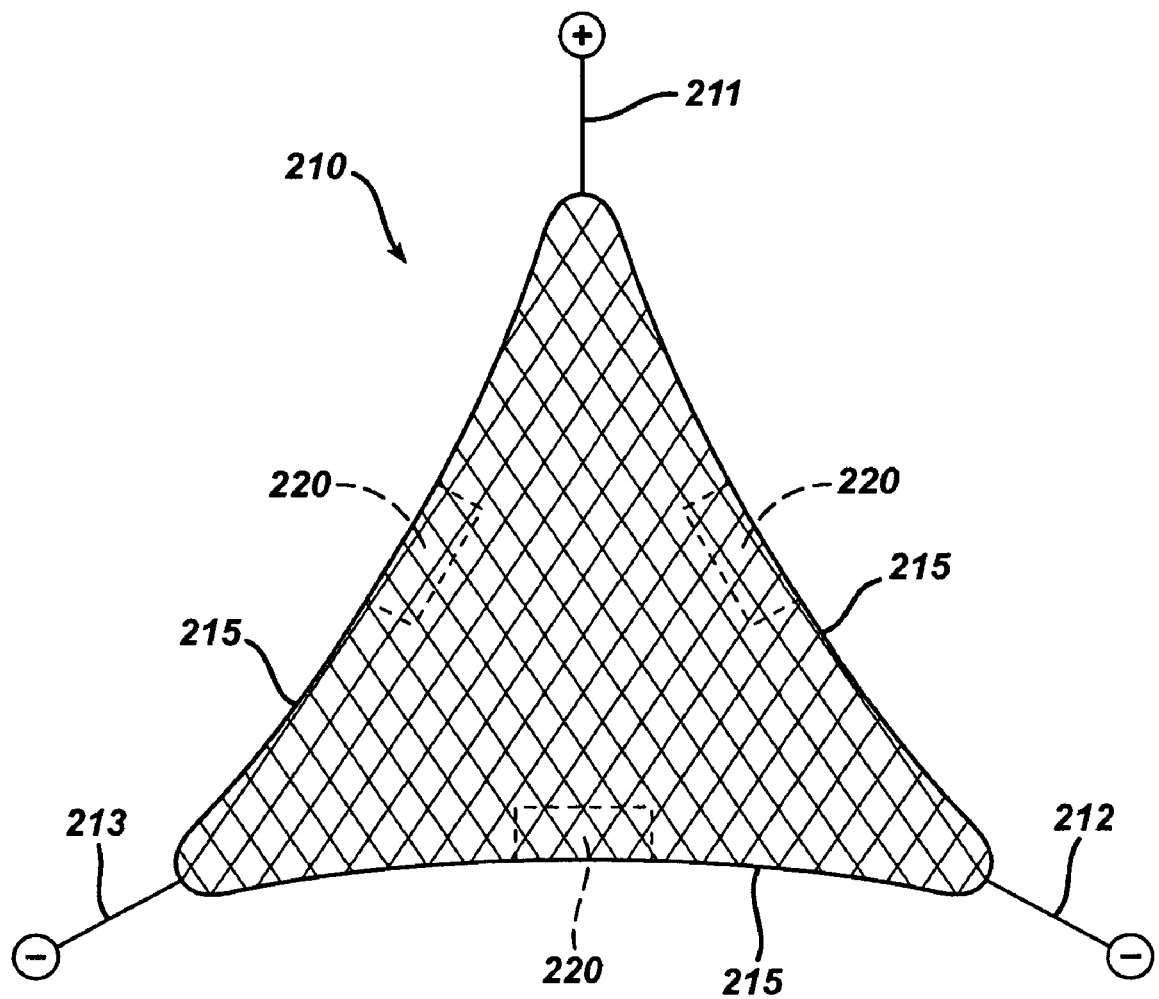
FIG. 3 illustrates a generally triangular-shaped cardiac assist device wrap according to the invention.

FIGS. 2 and 3 illustrate various embodiments of a cardiac assist device 110 according to the invention. The cardiac assist device 110 is a wrap comprised of a flexible bio-compatible material. In FIG. 2, the cardiac assist device is generally rectangularly-shaped, whereas in FIG. 3 the cardiac assist device is generally tri-lateral or triangularly-shaped. The skilled artisan should appreciate that any one of a variety of shapes may comprise the wrap of the cardiac assist device according to the invention provided sufficient material to fit and wrap the heart closely is provided. Regardless of shape, it should be appreciated by a skilled artisan that the wrap may be any such type of plastic, elastic or metal fiber sheet known in the art for such cardio-surgical procedures as described herein, it may be woven or non-woven, and does not have to be meshed.

Referring to FIG. 2, the mesh sheet 110 has a first suture tether 111, a second suture tether 112, a third suture tether 113, a fourth suture tether 114, and an outer seam 115. The outer seam 115 generally extends along the perimeter of the rectangularly-shaped mesh sheet 110. Each tether extends from one corner of the rectangularly-shaped mesh sheet 110. Each tether is provided with its own magnetic charge. Thus, the first tether 111 has a first magnetic charge and the second tether 112 has a second magnetic charge, the first magnetic charge being opposite that of the second magnetic charge. The third tether 113 preferably has a charge similar to the first magnetic charge, and the fourth tether 114 has a charge similar to the second magnetic charge. In this manner, similarly charged tethers extend from diagonally opposite corners of the mesh sheet 110, and are available for coupling with correspondingly magnetically charged capture instruments, as discussed in further detail below with respect to FIGS. 4-9. In some embodiments according to the invention, magnets 120 (shown in dashed lines) may be placed along the periphery of the mesh sheet 110 near the outer seam 115. These magnets 120 can be used to secure the mesh sheet 110 to anchoring devices 500 as discussed in more detail below with reference to FIGS. 10-15.

FIG. 3 similarly illustrates a cardiac assist device having tethers 211, 212 and 213 placed at extremities of the triangularly-shaped wrap 210. Each tether is provided with a magnetic charge. The tethers 211-213 are thus available for coupling with correspondingly magnetically charged capture instruments. An outer seam 215 extends along the perimeter of the triangularly-shaped mesh sheet 210. Some embodiments place magnets 220 (shown in dashed lines) along the periphery of the mesh sheet 210 near the outer seam 215. These magnets 220 can be used to secure the mesh sheet 210 to anchoring devices 500 similar to as referred to above.

Figure 4:
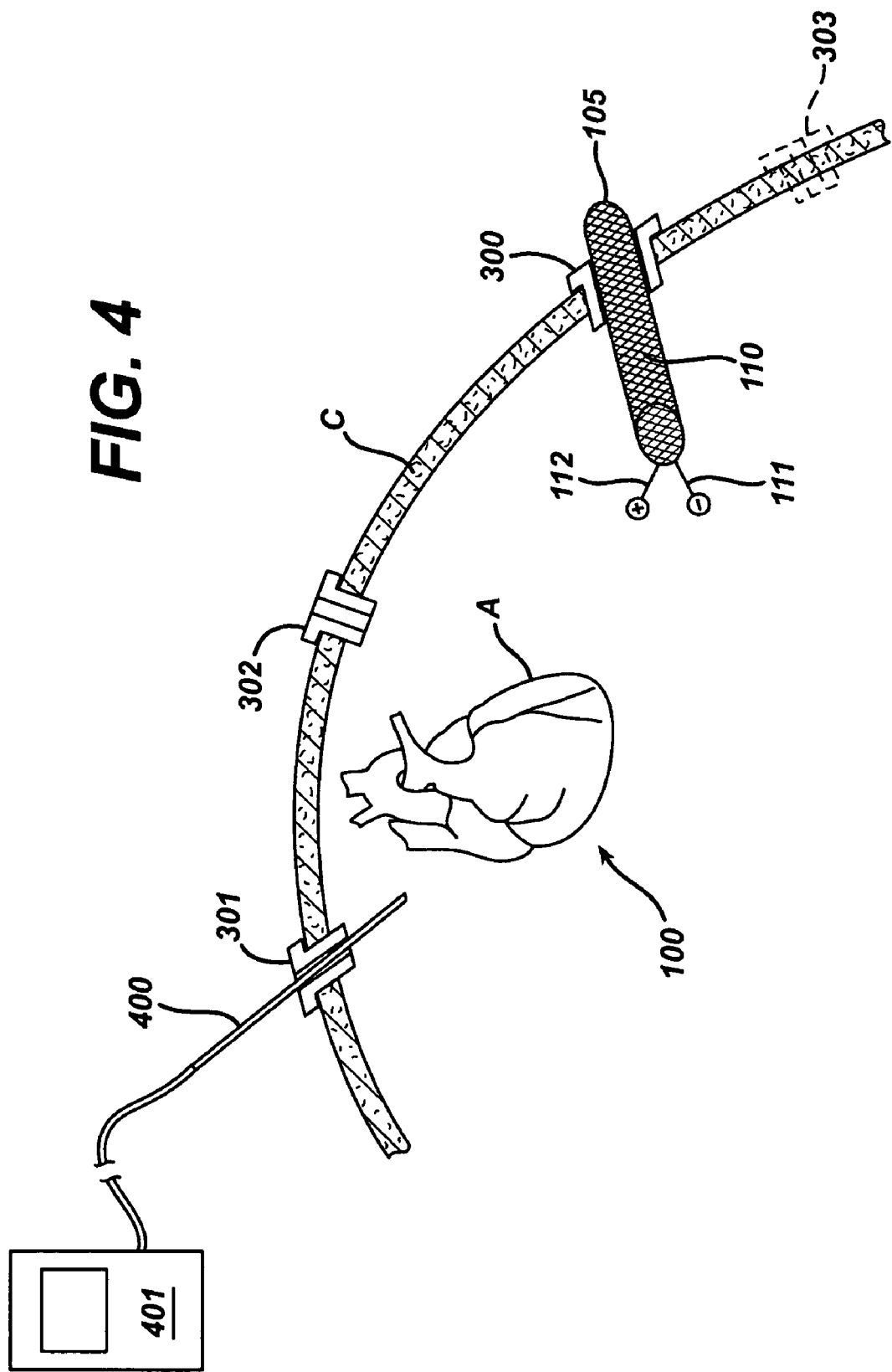
FIG. 4 illustrates various insertion ports provided through a chest wall of a body for inserting, manipulating and withdrawing various instruments and devices relative to a chest cavity according to the invention.
Figure 5:
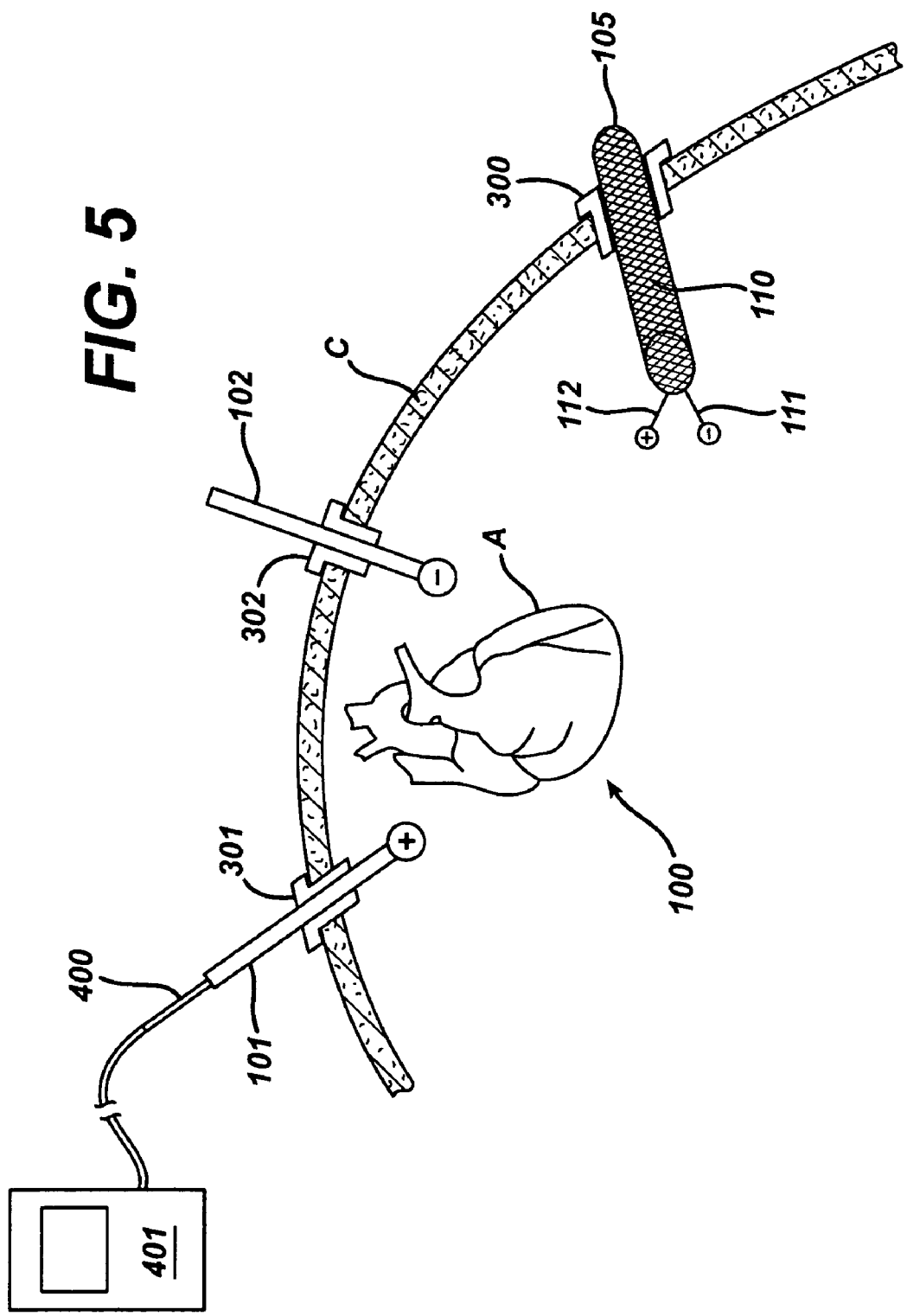
FIG. 5 illustrates occupied insertion ports deploying a delivery tube, capture instruments and an endoscope in the chest cavity according to one embodiment of the invention.
Figure 6:
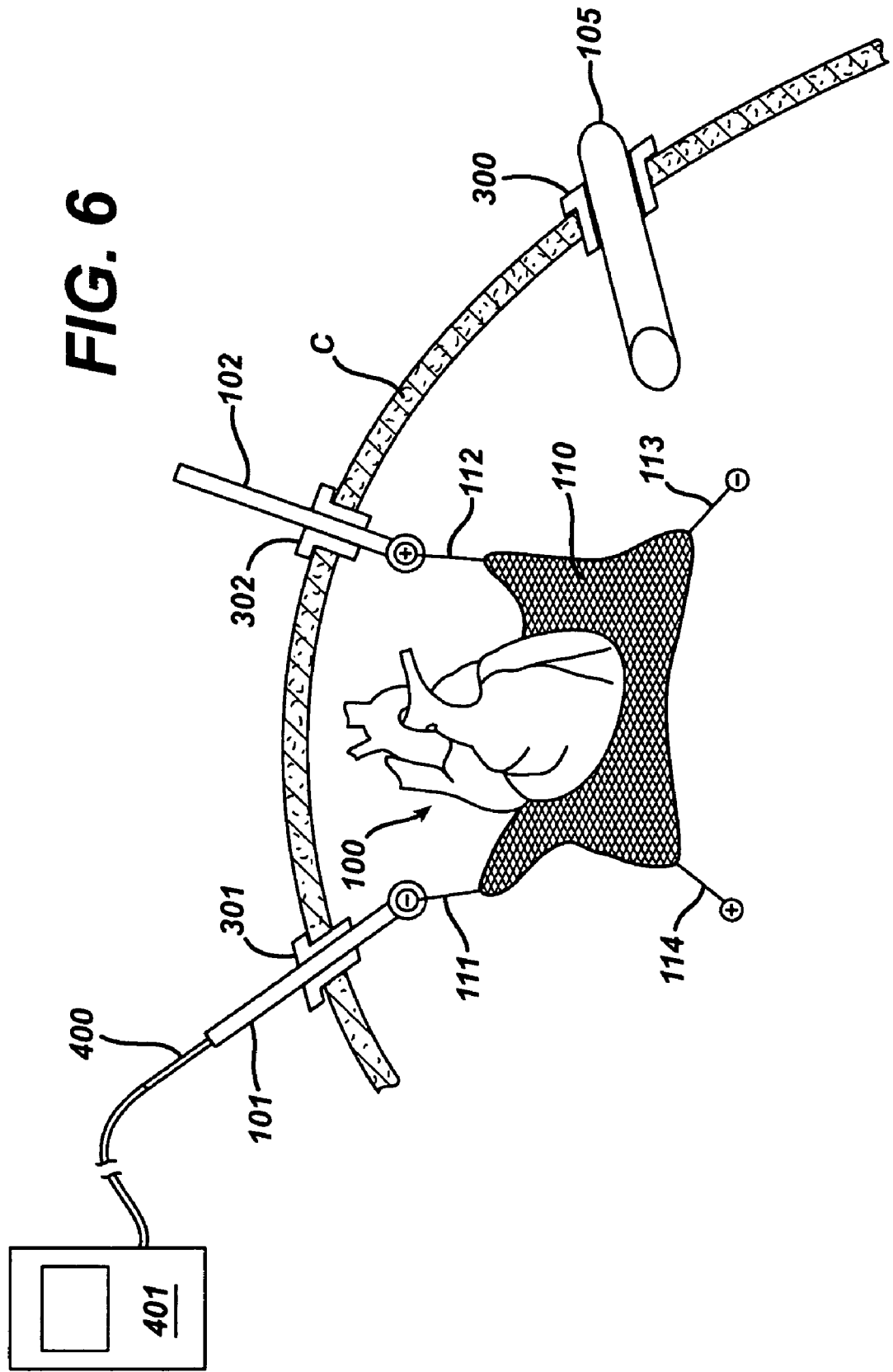
FIG. 6 illustrates one embodiment of the cardiac assist device fully withdrawn from the delivery tube according to the invention.

With reference now to FIGS. 4-6, a rectangularly-shaped cardiac assist device 110 is placed in a delivery tube 105. The first and second suture tethers 111, 112 of the cardiac assist device 110 protrude slightly from an open end of the delivery tube. The capture and maneuvering of these tethers 111, 112 for the eventual withdrawal of the mesh sheet from the delivery tube is made easier, as discussed further below, due to their slight protrusion from the delivery tube. The delivery tube 105, with the cardiac assist device 110 contained therein, is then inserted through an opening or port 300 provided in a chest wall C of a patient. The port 300 may be a trocar tube, for example, or other access means known in the art that permits insertion and withdrawal therethrough of instruments and/or devices, such as the delivery tube 105. Alternatively, port 300 may simply be an opening within the chest wall or below the chest wall of the patient (subxyphoid). In either case, the opening may be held open with tape or some other retraction device. Using delivery tube 105 and port 300, the cardiac assist device 110 can be inserted into the chest cavity and placed near the apical region A of the heart 100. Alternatively, tethers 111, 112 may be disposed within delivery tube 105 in a first position as tube 105 is introduced into the patient's body, and then moved by a pusher element (not shown) disposed at least partially within delivery tube 105 to a second position, such that the magnetic charges of tethers 111, 112 are exposed at the distal end of tube 105. Tethers 111, 112 may be formed of a flexible or shape memory material, such as nitinol, such that when tethers 111, 112 are moved distally the magnetic charges of tethers 111, 112 assume a predetermined position relative to the distal end of the delivery tube.

As shown also in FIG. 4, additional openings or ports 301, 302, and optionally port 303 (shown in dashed lines) may be provided through the chest wall C. As before with respect to port 300, these additional ports 301-303 may be trocar tubes, for example, or other access means known in the art that permit insertion and removal of various medical instruments and devices therethrough, such as simple incisions. Any of the provided ports may be used to insert an endoscope, or other visualizing means known in the art, so that a medical professional may view the insertion and withdrawal of the delivery tube 105, for example, or the various other procedures performed according to the invention as they occur. The ports 300-303 also accommodate the manipulation of the various instruments or devices inserted therethrough.

FIG. 4 shows schematically an endoscope 400 inserted through port 301, for illustrative purposes only. The endoscope, or other visualization means, is connected to a video display monitor or system 401 as is known in the art. The video display system 401 is external to the body permitting the medical professional to view the interior of the chest cavity where the endoscope or other visualization means is positioned.

FIG. 5 illustrates an embodiment according to the invention where the optional port 303 is not provided. In such a case, the endoscope 400, for example, as the visualizing means, is inserted into one of ports 301 or 302 to view the insertion of the delivery tube 105 through the chest wall. In FIG. 5, for example, the endoscope is inserted in port 301. It should be appreciated of course, that either of the ports 301, 302 is ideally equally available for insertion of an endoscope in this manner. Thereafter, capture instruments 101 and 102 are inserted through ports 301 and 302, respectively, even as the endoscope 400 remains positioned in one of the ports 301 or 302. Meanwhile, proximal portions of the capture instruments 101, 102 and endoscope 400 remain outside of the chest wall and available for manipulation by the medical professional. Because the endoscope remains in place through one of the ports 301 or 302, the medical professional is able to see the delivery tube 105 and the tethers 111, 112 protruding from the open end of the delivery tube near the apical region A of the heart, as well as the capture instruments 101, 102.

As shown in FIG. 6, the capture instruments 101, 102 are maneuvered by the medical professional to magnetically couple with the oppositely charged tether 111, 112, respectively. After magnetic coupling occurs, the capture instruments 101, 102 and tethers 111, 112 are further maneuvered to withdraw the cardiac assist device 110 fully from the delivery tube 105. Cardiac assist device 110 can be either pulled from tube 105 or pushed by a pusher element, or both. The endoscope 400 inserted through port 301, for example, as shown in FIG. 6, permits the medical professional to view the location of the tethers 111, 112 and the capture instruments 101, 102 in order to accomplish their coupling securely. Likewise, the endoscope permits ready viewing of the cardiac assist device 110 as it is being withdrawn from the delivery tube 105. Thereafter, the capture instruments 101, 102 and tethers 111, 112 position the cardiac assist device 110 under the heart and the empty delivery tube 105 is removed from the chest cavity through port 300.

Figure 7:
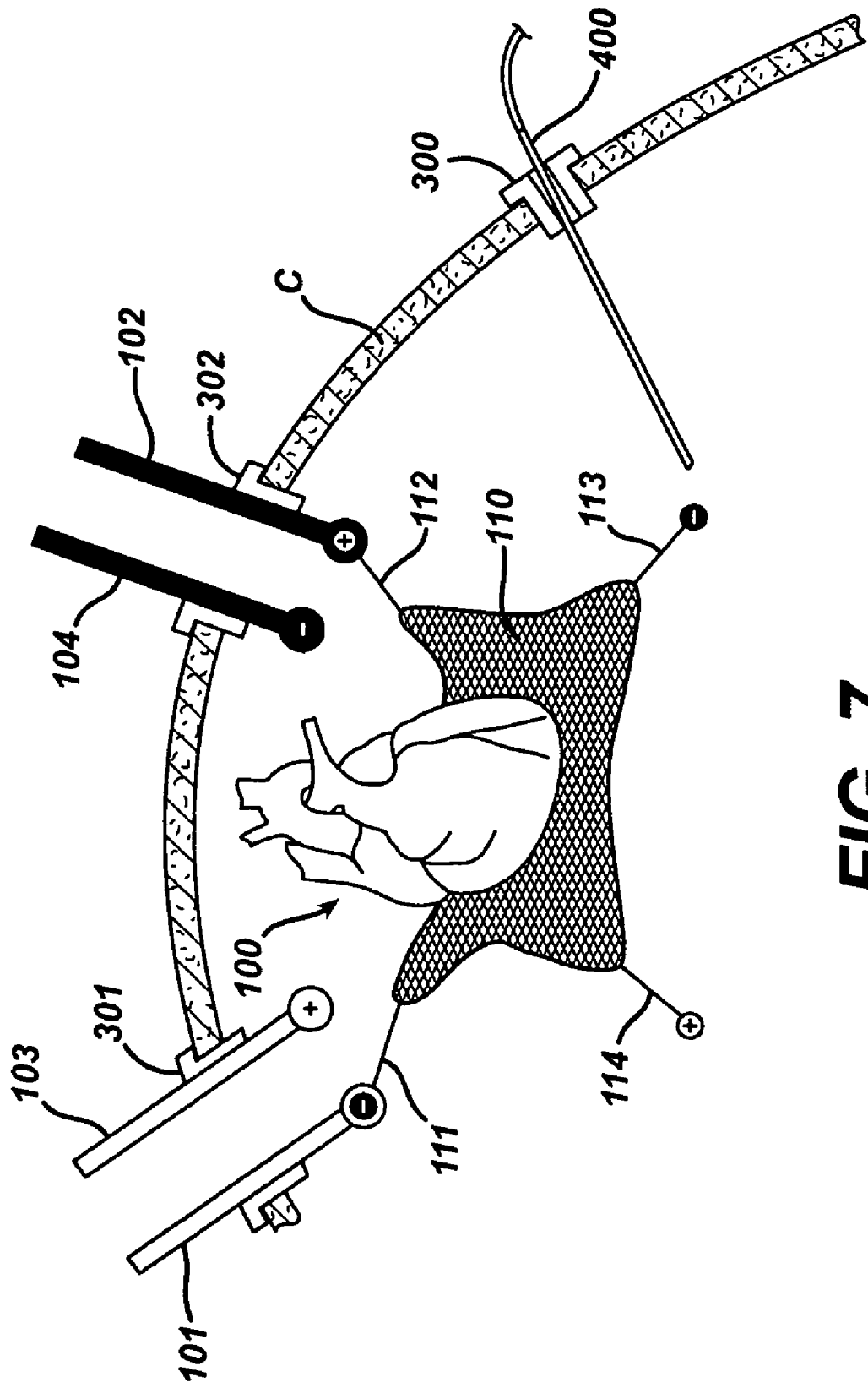
FIG. 7 illustrates exaggerated insertion ports through which pairs of capture instruments are deployed according to the invention.

Removal of the empty delivery tube 105 through port 300 occurs by grasping the closed end of the delivery tube 105 using, for example, surgical clamps, forceps, or other grasping or suction means (not shown) as are known in the art. The grasping or suction means are used to pull the delivery tube 105 through the port 300 and out of the chest cavity of the being. Once the delivery tube 105 is removed, the port 300 becomes available to receive the endoscope, or other visualizing means, that has thus far been inserted to the chest cavity through one of ports 301 or 302. FIG. 7 illustrates the insertion of the endoscope 400, for example, through port 300.

Of course, where the optional port 303 (FIG. 4) is provided, the endoscope, or other visualizing means, may be initially inserted through the optional port 303. In this case, the endoscope need not be transferred into the port 300 vacated by the removal of the delivery tube 105 from port 300. Rather, removal of the delivery tube 105 from port 300 permits port 300 to be removed as well using conventional port removal techniques. In this embodiment, therefore, viewing of the procedures according to the invention occurs via the endoscope or other visualizing means inserted through optional port 303. The artisan should appreciate that insertion of the endoscope or other visualizing means into the optional port 303 is achieved similarly to the insertion of the endoscope 400 through either of ports 300-302, thus illustration of the insertion of the endoscope or other visualizing means through optional port 303 is omitted.

Referring still to FIG. 7, additional capture instruments 103 and 104 are inserted through ports 301 and 302, respectively, even as capture instruments 101 and 102 remain inserted through ports 301 and 302. FIG. 7, for example, shows ports 300, 301 and 302 in an exaggerated view to better illustrate the insertion of capture instruments 101 and 103 through port 301, and the insertion of capture instruments 102 and 104 through port 302. The endoscope, or other visualizing means, is inserted through port 300 in FIG. 7. As before, proximal portions of each capture instrument 101-104 extend outside the chest wall and are available to the medical professional to maneuver as desired.

Figure 8:
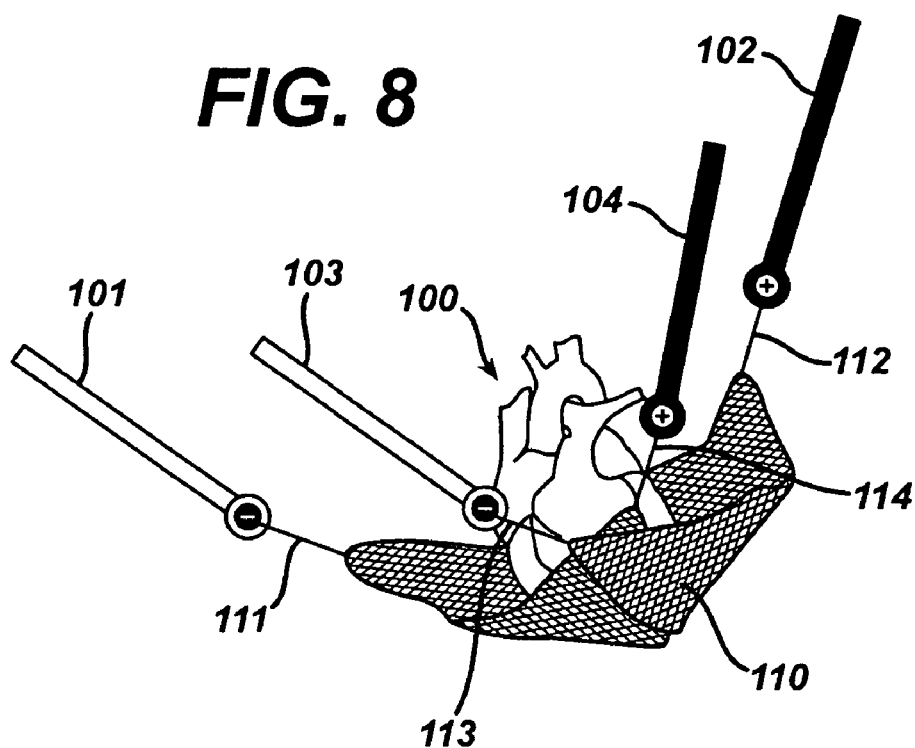
FIG. 8 illustrates magnetically coupled capture instruments and tethers undergoing a wrapping sequence according to the invention.
Figure 9:
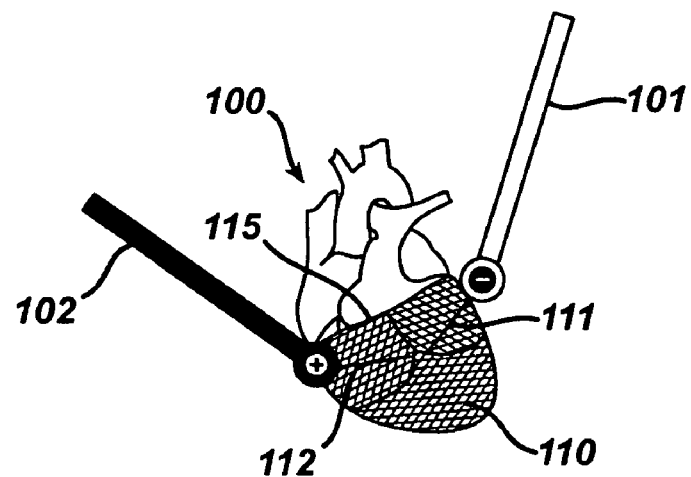
FIG. 9 illustrates a further stage of the wrapping sequence of FIG. 8 according to the invention.

Referring now to FIGS. 7-9, wherein the chest wall C, ports 300-302 and endoscope 400 are omitted from illustration in FIGS. 8 and 9 but understood to exist consistent with that shown in FIG. 7, the capture instruments 101-104 are each provided with a magnetic charge at their respective distal ends in order to couple with a corresponding one of the tethers 111-114 extending from the cardiac assist device 110. For example, as shown in FIG. 8, the first capture instrument 101 is magnetically charged with the second magnetic charge to couple with the correspondingly oppositely charged first tether 111, whereas the second capture instrument 102 is magnetically charged with the first magnetic charge to couple with the correspondingly oppositely charged second tether 112. Similarly, the third capture instrument 103 is coupled with the third tether 113, and the fourth capture instrument 104 is coupled with the fourth tether 114. In this manner, all of the tethers 111-114 are magnetically coupled to a correspondingly oppositely charged capture instrument. The coupling of the capture instruments 101-104 with the tethers 111-114 is readily viewed by the endoscope 400 inserted now through port 300, for example.

By designating the magnetic charges for the tethers and instruments, the tethers are more reliably coupled with a correspondingly charged capture instrument. This arrangement increases the ability of the coupled instruments and tethers to maneuver the mesh sheet around the heart, and minimizes the likelihood of tethers breaking away from the instruments when maneuvering of the mesh sheet is attempted. Each magnetic component is provided with sufficient strength to reduce the occurrence of an unintended release of a tether from a capture instrument. As also shown in FIGS. 7-9, for example, color coding of the capture instruments 101-104 and tethers 111-114 may be used in addition to the magnetic coupling designations to identify which instrument corresponds to which tether, and to identify the order of maneuvering the instruments and tethers when coupled. As a result, a more reliable fit of the mesh sheet around the heart may be achieved.

Referring still to FIGS. 8 and 9, the artisan should appreciate that proximal portions of the capture instruments 101-104 extend externally beyond the chest wall of the being and are available to the medical professional for manipulation. The capture instruments 101-104 and respective tethers 111-114 magnetically coupled thereto, are thus maneuvered in a sequence by the medical professional that wraps the mesh sheet 110 around desired portions of the heart 100. The medical professional is able to view the manipulation of the capture instruments and respective tethers and better control the wrapping sequence as a result of the endoscope positioned in the port 300, or optional port 303 where provided.

In the embodiment shown in FIGS. 8 and 9, the magnetically coupled third capture instrument 103 and tether 113 are first maneuvered towards the first capture instrument 101, and the magnetically coupled fourth capture instrument 104 and tether 114 are then maneuvered towards the second capture instrument 102. The third capture instrument 103, fourth capture instrument 104, and their respectively coupled tethers 113, 114 are then pulled so that the associated corners of the mesh sheet 110 overlap one another and wrap around desired portions of the heart 100. Then, as shown in FIG. 9, the magnetically coupled first capture instrument 101 and tether 111 are maneuvered toward the second capture instrument 102, and the magnetically coupled second capture instrument 102 and tether 112 are maneuvered toward the first capture instrument 101. More specifically, the first capture instrument 101 and the second capture instrument 102 are pulled so that the corners of the mesh sheet 110 attached to tethers 111, 112 overlap one another and wrap snugly around the heart 100. Desired portions of the heart 100 are thus enclosed in the mesh sheet 110. The entire wrapping procedure may be viewed using the endoscope 400.

Once located at a desired position around the heart, the mesh sheet 110 is secured to the heart. For example, the coupled instruments 101-104 and respective tethers 111-114 may be manipulated additionally to suture the mesh sheet directly to the heart using known endoscopic suturing instruments. The endoscopic suturing instruments can utilize one or more of the same ports 300-302 previously occupied by the capture instruments or delivery tube. In this manner, the medical professional is able to view the suturing procedure using the same endoscope, or other visualizing means, already inserted in one or more of the ports 300-302, or optional port 303 where provided. In FIG. 9, for example, the suturing may be done at the seam 115, and where overlaps of the material of the cardiac assist device 110 occur. Once the mesh sheet is sutured to the heart, the capture instruments 101-104 are detached from the tethers 111-114 and, together with the endoscope and any suturing instruments, are removed from the chest cavity.

Figure 10:
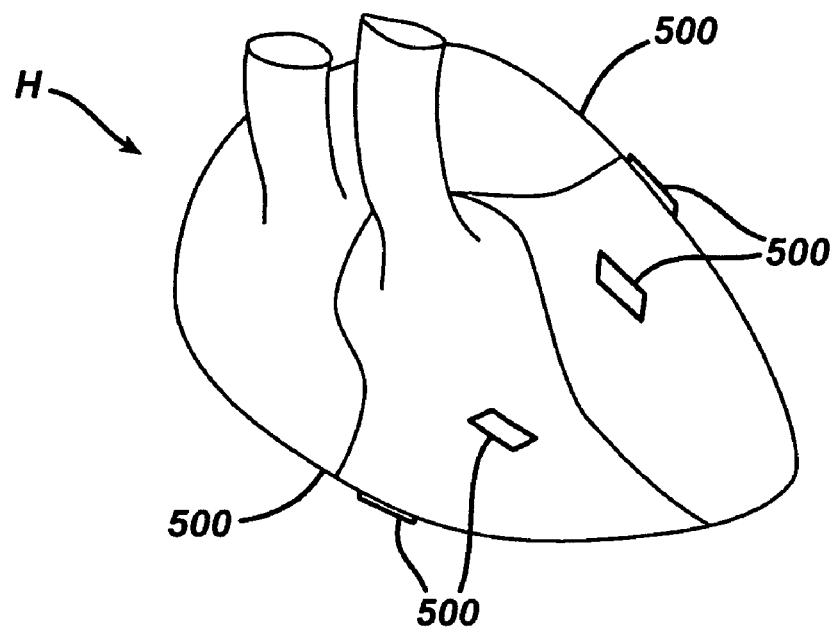
FIG. 10 illustrates anchoring devices placed at various locations on the surface of the heart according to the invention.

Alternatively, as shown in FIG. 10, anchoring devices 500 may be placed at designated locations and secured onto the surface of the heart H. The anchoring devices 500 are preferably placed and secured on the surface of the heart prior to delivery of the delivery tube 105 and cardiac assist device 110 in order to minimize clutter in the chest cavity as subsequent procedures are performed. It should be appreciated, however, that placement of the anchoring devices can occur at anytime prior to the cardiac assist device 110 being secured thereto.

Figure 18:
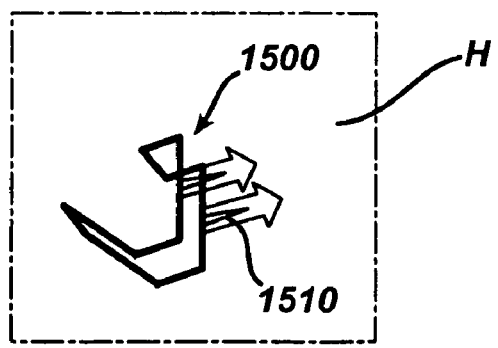
FIG. 18 illustrates a self-anchoring anchoring device according to the invention.

FIG. 10 illustrates generally as many as six anchoring devices 500 placed on the surface of the heart. The artisan should appreciate, however, that as few as one anchoring device 500 could provide a means of securing the cardiac assist device to the heart. Of course, it should be further appreciated that more than six anchoring devices may also be used. FIG. 10, in partial view for example, illustrates two anchoring devices 500 on the posterior side of the heart, two anchoring devices 500 on the anterior side of the heart, and one anchoring device 500 on each lateral side of the heart. Sutures, u-clips, staples adhesives, or other securing means known in the art are used to secure each anchoring device to the heart. Of course, the artisan will appreciate that different anchoring devices may be used at different locations of the heart in order to more easily secure the anchoring devices to the heart. For example, anchoring devices may be sutured to lateral and anterior sides of the heart as in FIG. 10, whereas self-anchoring devices (FIG. 18) may be used on the posterior side of the heart. The self-anchoring device 1500 of FIG. 18 includes a barb 1510 that projects from the anchoring device for attaching to the heart. The cardiac assist device may thus be secured to the various anchoring devices that are separately secured directly to the heart.

Figure 11:
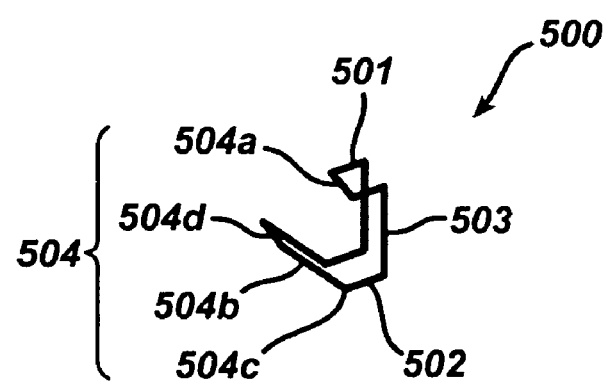
FIG. 11 illustrates one embodiment of a non-magnetic anchoring device according to the invention.

FIG. 11 shows one embodiment of an anchoring device 500 according to the invention. The anchoring device shown in FIG. 11 is a non-magnetic frame-like member comprised of a top 501, a bottom 502, a back 503, and a front 504. The front 504 is further comprised of a lip 504a, and a pivotable flange 504b. The pivotable flange 504b has a hinged end 504c attached to the bottom 502 of the anchoring device, and a free end 504d opposite the hinged end. The pivotable flange 504b engages the lip 504a to close the front of the anchoring device 500. Of course, the artisan will appreciate that the anchoring device could as well be comprised of a first member pivotable with respect to a second member that is secured to the heart, whereby the first and second members engage one another to close and capture a part of the cardiac assist device wrap thereby securing the wrap to the anchoring devices.

Figure 12:
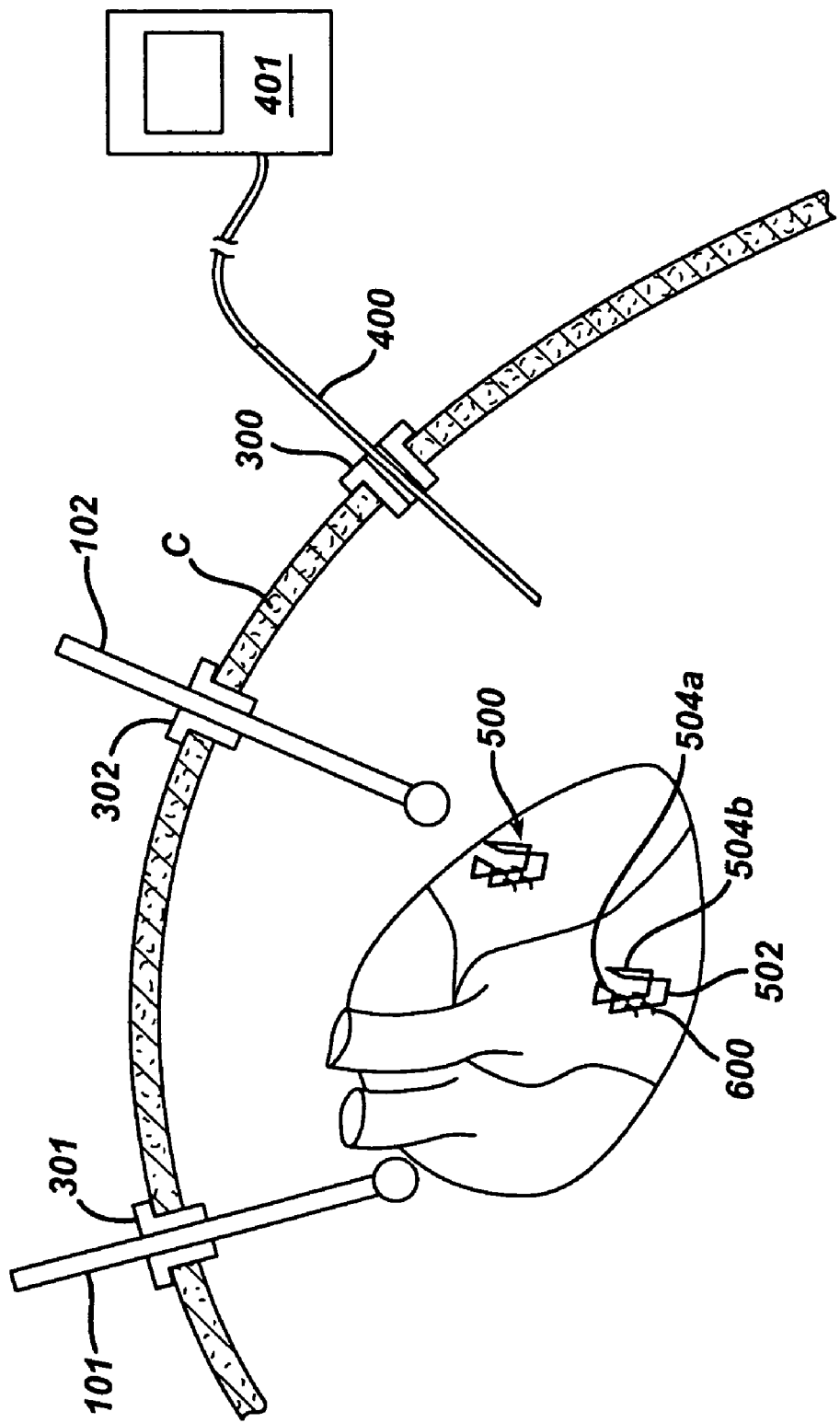
FIG. 12 illustrates a technique for placing an anchoring device on the heart according to the invention.

In practice, as shown in FIG. 12, the anchoring devices 500 are inserted into the chest cavity through one of the ports 300-302. The anchoring devices 500 are then maneuvered in turn and placed on the heart using one or more of the capture instruments 101-104 (only capture instruments 101, 102 shown for clarity), the capture instruments 101-104 having been inserted through the ports 301, 302 as discussed above. The artisan should appreciate that the use of fewer instruments in the chest cavity provides a less cluttered working environment with greater maneuverability of the instruments involved in the procedures according to the invention. As before, the endoscope 400 remains inserted through one of ports 300-302, or optional port 303, to permit the medical professional to view the procedures as they occur. Where the anchoring devices are being placed on a posterior side of the heart, a suction instrument (not shown), as is known in the art, may be additionally inserted through one of ports 300-302 in order to lift and/or stabilize the heart slightly while the endoscopic placement of the anchoring devices 500 on the posterior side of the heart occurs. Alternatively, a fork-like instrument (not shown) as is known in the art, could be used to lift or stabilize the heart as well.

Referring still to FIG. 12, once placed as desired on the surfaces of the heart, the anchoring devices 500 are each endoscopically secured directly to the heart using conventional securing means such as sutures, U-clips, staples, adhesives, or other suitable device 600. The suction instrument referred to above may also be used to lift the heart slightly when securing the anchoring devices to the posterior side of the heart. Endoscopic suturing instruments, for example, as are known in the art may be inserted through ports 300-302 to secure the anchoring devices 500 to the heart in turn. As before, the endoscope 400, or other visualizing means, remains in the chest cavity through one of ports 300-302, or optional port 303, and permits the medical professional to view the securing procedure as it occurs.

Figure 13A:
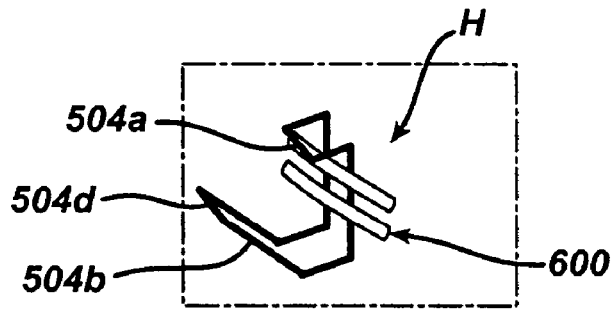
FIGS. 13a-13c illustrate the non-magnetic anchoring device of FIG. 11 at various stages of engagement wherein the cardiac assist device is folded over and clamped by the anchoring device to secure the cardiac assist device to the heart according to the invention.
Figure 13B:
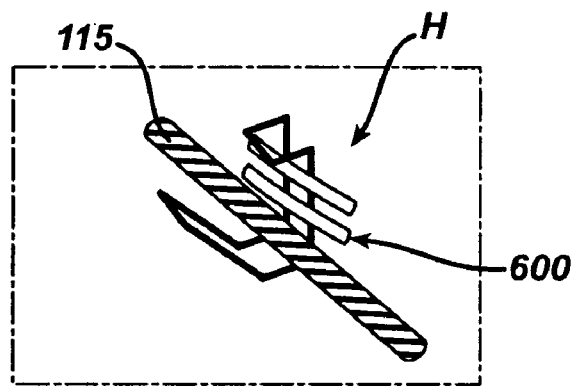
Figure 13C:
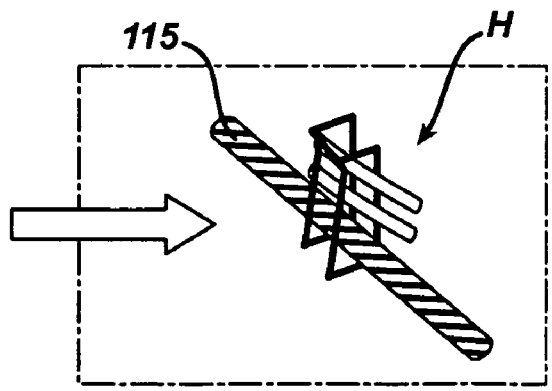

Referring now to FIGS. 13a-13c, wherein the chest wall, various ports, instruments and endoscope are omitted from illustration for clarity, though it is understood that all are present as needed as before. More particularly, FIG. 13a shows an exemplary anchoring device 500 secured by securing means 600 to the surface of the heart H. In FIG. 13a, the pivotable flange 504b is in an open position, i.e. not engaging the lip 504a. In FIG. 13b, an upper seam 115 and some material of the cardiac assist device 110 is endoscopically manipulated using the capture instruments 101-104, for example, to fold the seam 115 and material over the free end 504d of the flange 504b. The flange 504b is then endoscopically manipulated to engage the lip 504a of the anchoring device 500 thereby closing the anchoring device (FIG. 13c)

and clamping the material of the cardiac assist device 110 therebetween the engaged lip 504a and free end 504d of the anchoring device. Other portions of the seam 115 and material of the cardiac assist device 110 are then clamped between the similarly engaged lip 504a and free end 504d of each anchoring device 500. In this manner, the cardiac assist device is thus securely positioned about the heart.

Figure 14A:
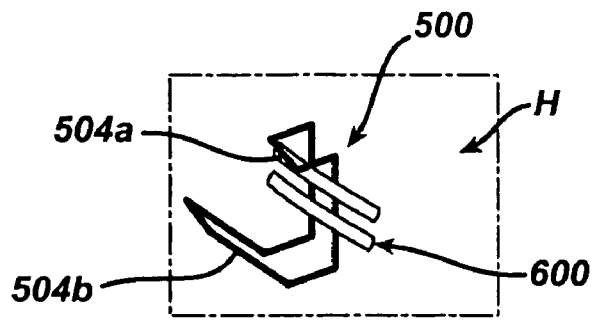
FIGS. 14a-14c illustrates the non-magnetic anchoring device of FIG. 11 at various stages of engagement wherein tethers are tied or sutured to the anchoring device to secure the cardiac assist device to the heart according to the invention.
Figure 14B:
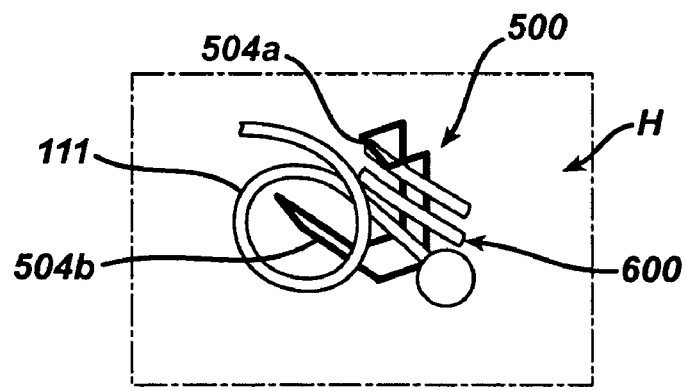
Figure 14C:
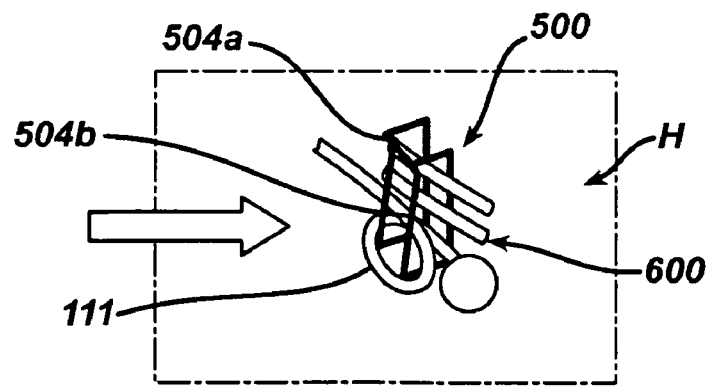

Referring now to FIGS. 14a-14c, another embodiment of securing the cardiac assist device 110 to the anchoring device 500 of FIG. 11 comprises manipulating the magnetically coupled capture instruments 101-104 and tethers 111-114 in order to tie (FIG. 14b) each tether to one of the anchoring devices 500 and then engaging the flange 504b with the lip 504a (FIG. 14c) to close the anchoring device as before. Each tether is tied in turn to one of the anchoring devices in this manner in order to secure the cardiac assist device to the heart. As before, the endoscope 400 is positioned through one of ports 300-302, or optional port 303 to view the procedures as they occur.

Figure 15:
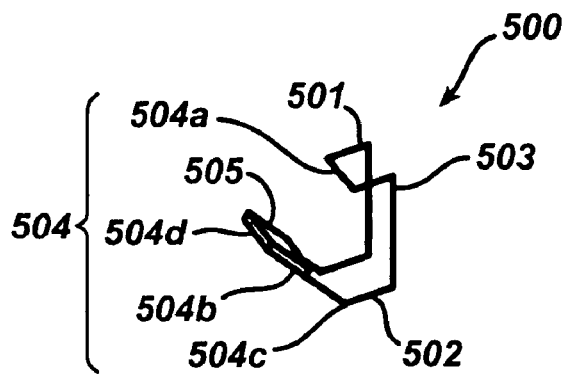
FIG. 15 illustrates one embodiment of a magnetic anchoring device according to the invention.

FIG. 15 illustrates another embodiment of the anchoring device 500, wherein like numerals refer to like components as compared to the anchoring device shown in FIGS. 11-14c. The only difference between the embodiments of FIGS. 11 and 15 is that a magnetic plate 505 extends across an upper portion of the pivotable flange 504b in the embodiment shown in FIG. 15.

Figure 16A:
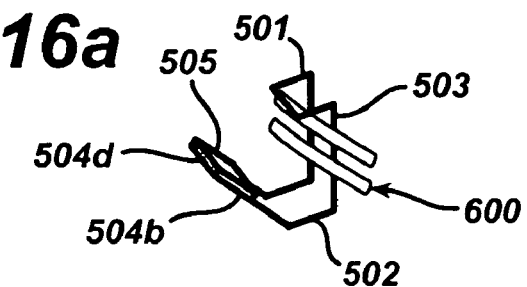
FIGS. 16a-16d illustrate the magnetic anchoring device of FIG. 15 at various stages of engagement wherein the cardiac assist device is magnetically coupled to the anchoring device to secure the cardiac assist device to the heart according to the invention.
Figure 16B:
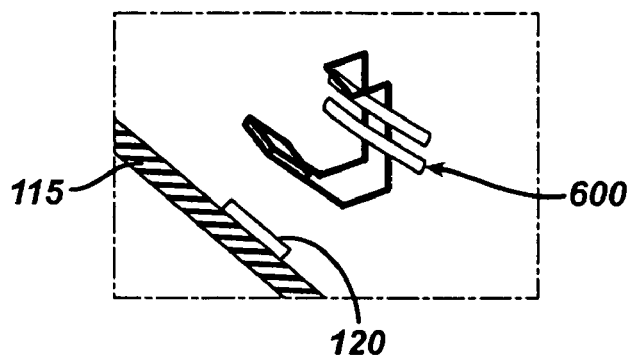
Figure 16C:
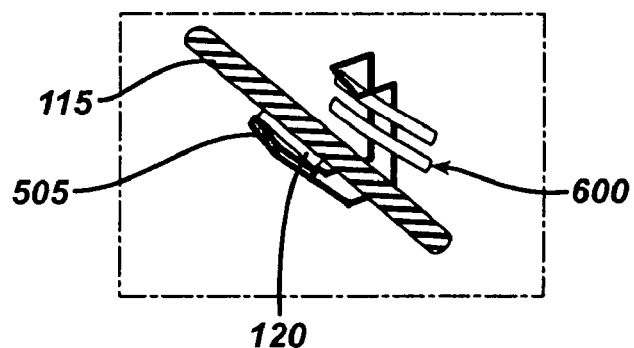

Referring now to FIGS. 16a-16c, wherein the chest wall, ports, instruments and endoscope are omitted from illustration but understood to exist as in FIG. 12, for example, the anchoring device 500 is placed and secured to the surface of the heart H similar to as described above with reference to FIG. 12. Sutures, clips, staples or other securing means 600 secure each anchoring device 500 in place. In FIG. 16a, the pivotable flange 504b of the anchoring device 500 is in an open position, i.e., not engaging the lip 504a. In FIGS. 16b and 16c, the upper seam 115 and some material of the cardiac assist device has been endoscopically manipulated to fold the seam 115 and magnet 120 of the cardiac assist device 110 over the free end 504d of the flange 504b. As a result, the magnet 120 of the cardiac assist device 110 aligns and magnetically couples with the magnetic plate 505 at the upper end of the flange 504b to secure the cardiac assist device thereto. The capture instruments 101-104, for example, or other conventional grasping instrument known in the art may be used to manipulate the seam 115, material and magnet 120 in this manner. The capture instruments 101-104, or other grasping instruments, are inserted through one or more of ports 300-302 as discussed above with reference to FIG. 12, for example.

Figure 16D:
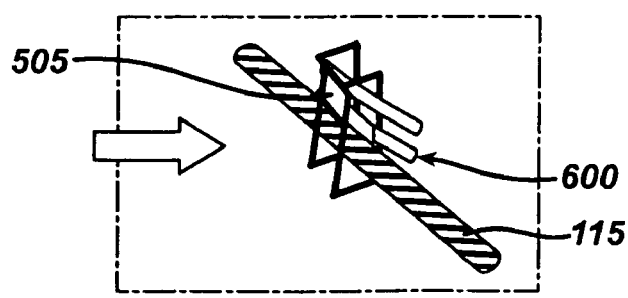

The flange 504b is then endoscopically manipulated by the capture instruments, for example, to engage the lip 504a of the anchoring device 500, thereby closing the anchoring device (FIG. 16d) and clamping the material of the cardiac assist device therebetween the engaged lip 504a and free end 504d of the flange 504b. Other portions of the seam 115 and cardiac assist device material with magnets 120 are then aligned, coupled and clamped similarly. In this manner, the cardiac assist device is securely positioned about the heart.

Figure 17:
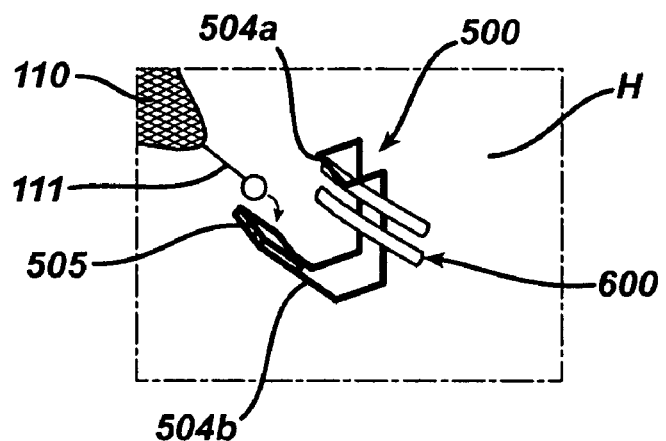
FIG. 17 illustrates tethers magnetically coupled with a corresponding magnetic plate of the anchoring device of FIG. 15 according to the invention.

FIG. 17 illustrates the magnetic anchoring device 500 of FIG. 15, for example, secured to the heart H by sutures 600, or other known securing means. FIG. 17 further illustrates an exemplary one of the magnetically charged tethers 111-114 aligned and coupled with the magnetic plate 505 of the anchoring device 500 in order to secure the cardiac assist device 110 (shown in partial view) to the heart. Once coupled with the plate 505, the flange 504b of the anchoring device 500 is closed as before. As before, the capture instruments and endoscope are inserted through various ports 300-302, or optional port 303, in order to manipulate and align the tethers to align and couple appropriately with the magnetic plate of the anchoring device. In this manner, each tether is secured to the anchoring device and the cardiac assist device is secured about the heart as desired.

The various embodiments of the invention as described hereinabove are illustrative only and not intended to be limitations of the various aspects of the invention. Various other combinations of the present invention are possible, in which different types of medical instruments are used for capture of the suture tethers. Further, the tethers may be suture tethers, or any means known in the art to manipulate, align, couple, tie or otherwise secure the cardiac assist device, or other cardiac implant, around the heart. Any means other than magnets that provide a magnetic charge may be used for the capture instruments, suture tethers or other magnetic components of the invention. The skilled artisan will appreciate that the combination of magnetic charges described herein are exemplary only, and that various other charge arrangements are available without deviating from the spirit and scope of the invention.

The wrap of the invention is not limited by the mesh sheet 110, and may comprise various other jackets and/or bags as would be known to one of ordinary skill in the art. Further, the wrap may be any type of flexible bio-compatible material including but not limited to plastic, elastic, or metal fiber known in the art as suitable for such procedures, it may be woven or non-woven, and does not have to be meshed. For example, the wrap may be a fabric like that described in U.S. Pat. No. 6,682,476, or materials such as those described in U.S. Pat. No. 6,595,912, which are hereby incorporated by reference. The wrap is preferably made of a biologically compatible material, and may be made of various shapes, such as, but not limited to, a rectangular, square, triangular or tri-lateral shape wherein tethers extend from corners or extremities thereof.

While there has been shown and described what is considered to be preferred embodiments of the invention, it will, of course, be understood that various modifications and changes in form or detail could readily be made without departing from the spirit or scope of the invention. For example, while the invention has been described as being utilized in an endoscopic procedure, the systems described can also be used in an open chest or hybrid procedure that would not rely solely upon openings in a patient's chest or below the patient's chest to deploy the system. It is therefore intended that the invention be not limited to the exact forms described and illustrated herein, but should be constructed to cover all modifications that may fall within the scope of the appended claims.

What is claimed is:

1. A system for placing a cardiac assist device on at least a portion of a heart, said system comprising:
   a wrap adapted to surround at least the portion of the heart;
   at least one tether extending from the wrap, each tether having a magnetic charge; and
   at least one instrument having a magnetic charge, each of the at least one instrument magnetically coupling with a corresponding one of the at least one tether, each of the at least one instrument further comprising a proximal portion adapted to extend externally from a body cavity such that each magnetically coupled instrument and tether are maneuverable to place the cardiac assist device at a desired position adjacent the heart.

2. The system of claim 1, wherein the wrap includes a seam along a periphery thereof.

3. The system of claim 1, wherein the wrap further comprises a flexible bio-compatible material adapted to envelope at least the portion of the heart.

4. The system of claim 3, wherein the wrap is comprised of one of an elastic, plastic, or metal fibers.

5. The system of claim 4, wherein said wrap comprises a mesh sheet.

6. The system of claim 5 wherein said mesh sheet comprises a rectangular mesh sheet having tethers extending from each corner thereof.

7. The system of claim 6, wherein the wrap further comprises at least one magnet integrated into the material along the seam of the wrap.

8. The system of claim 6, wherein tethers having similar magnetic charges extend from diagonally opposite corners of the rectangular mesh sheet.

9. The system of claim 5, wherein the wrap comprises at least a tri-lateral shape having tethers extending from at least three corners thereof.

10. The system of claim 1, wherein each instrument is color-coded to correspond to a similarly color-coded tether, the color coding being used to identify the coupling of each instrument to a corresponding one of the at least one tether.

11. The system of claim 1, further comprising at least one anchoring device configured to secure the wrap to the heart.

12. The system of claim 11, wherein each anchoring device is comprised of a first surface secured to the heart and a second surface pivotable with respect to the first surface to capture a portion of the wrap therein.

13. The system of claim 12, wherein each anchoring device further comprises a frame-like member having a top, a bottom, a back, and a front, the front being further comprised of a lip opposite a pivotable flange that engages the lip to close the anchoring device.

14. The system of claim 13, wherein each anchoring device is further comprised of a magnetic plate extending across an upper portion of the pivotable flange.

15. The system of claim 13, wherein the anchoring devices are non-magnetic.

16. The system of claim 1, further comprising a delivery tube inserted into the chest cavity and containing the wrap.

17. The system of claim 1, further comprising a visualizing means.

18. The system of claim 17, further comprising openings extending through a chest wall of a patient and configured to receive, withdraw and manipulate devices therethrough.

19. The system of claim 18, wherein the openings further comprise ports.

20. The system of claim 18, wherein the visualizing means is an endoscope.

21. A method for placing a cardiac assist device adjacent a heart, the method comprising:
providing a plurality of openings through a chest wall into a chest cavity of a being, the openings accommodating insertion, withdrawal and manipulation of various instruments and devices therethrough;
inserting a visualizing means into the chest cavity through one of the openings;
inserting a cardiac assist device into the chest cavity through one of the openings, the cardiac assist device having at least one tether, each tether having a magnetic charge;
separately inserting at least one instrument into the chest cavity through a corresponding one of the openings, each instrument having a magnetic charge at a distal end thereof, the magnetic charge being opposite the magnetic charge of a corresponding one of the at least one tether, each instrument also having a proximal portion extending exterior of the chest cavity for manipulation by a medical professional;
magnetically coupling each instrument with a corresponding tether and maneuvering each coupled instrument and tether to position the cardiac assist device at a desired position over the heart;
securing the cardiac assist device to the heart; and
removing the instruments and visualizing means from the chest cavity.

22. The method of claim 21, wherein the cardiac assist device further comprises a wrap made of a flexible bio-compatible material, the wrap having a seam along a periphery thereof.

23. The method of claim 22, wherein the wrap further comprises a rectangularly shaped mesh sheet having tethers extending from each corner thereof.

24. The method of claim 23, wherein tethers having similar magnetic charges extend from diagonally opposite corners of the rectangularly shaped mesh sheet.

25. The method of claim 22, wherein the wrap is a triangularly shaped mesh sheet having tethers extending from extremities thereof.

26. The method of claim 22, wherein the wrap includes magnets integrated into the material along portions of the seam.

27. The method of claim 22, further comprising:
securing the cardiac assist device to the heart at the desired position by one of suturing, clipping, stapling or adhering the device to the heart.

28. The method of claim 22, further comprising:
securing anchoring devices to the heart and then securing the cardiac assist device to the anchoring devices.

29. The method of claim 28, wherein a pair of anchoring devices are secured on a posterior side of the heart, a pair of anchoring devices are secured on an anterior side of the heart, and an anchoring device is placed on each lateral side of the heart.

30. The method of claim 29, wherein each anchoring device is secured to the heart by one of sutures, clips, staples or adhesives.

31. The method of claim 30, wherein the anchoring devices are comprised of a first surface secured to the heart, and a second surface pivotable with respect to the first surface to capture of portion of the wrap therein by pivoting the second surface to close the anchoring device.

32. The method of claim 30, wherein anchoring devices placed on a posterior side of the heart are self-anchoring devices having barbs projecting into the heart.

33. The method of claim 30, wherein each anchoring device is comprised of a frame-like member having a top, a bottom, a back, and a front, the front being further comprised of a lip opposite a pivotable flange that engages the lip to close the anchoring device.

34. The method of claim 33, wherein each anchoring device is non-magnetic and the tethers are secured thereto by manipulating the coupled capture instruments and tethers to tie each tether to a corresponding one of the anchoring devices.

35. The method of claim 33, wherein each anchoring device is non-magnetic and portions of the seam and material of the cardiac assist device are folded over the pivotable flange of the anchoring device which is then closed to secure the cardiac assist device thereto.

36. The method of claim 33, wherein each anchoring device is magnetic and the tethers are secured thereto by manipulating the coupled capture instruments and tethers to align and couple with a magnetic plate on a corresponding one of the anchoring devices.

37. The method of claim 33, wherein each anchoring device is magnetic and the cardiac assist device includes magnets integrated into the material along the seam thereof such that portions of the seam and material of the cardiac assist device are folded over the pivotable flange of the anchoring device to align and couple the magnets of the cardiac assist device with a corresponding magnetic plate positioned across an upper end of the pivotable flange of the anchoring device, the anchoring device then being closed to secure the cardiac assist device thereto.

38. The method of claim 22, further comprising: color coding the instruments and tethers to identify which instruments couples with which corresponding tether.

39. The method of claim 22, the method further comprising,
placing the cardiac assist device into a delivery tube and inserting the delivery tube into the chest cavity through one of the ports prior to inserting the at least one instrument in the chest cavity; and then
withdrawing the cardiac assist device from the delivery tube using the at least one instrument coupled to a corresponding one of the tethers.

40. The method of claim 22, wherein the wrap is secured to the heart once the wrap is located at the desired position adjacent the heart.

41. A cardiac assist device comprising:
a wrapping means adapted to surround at least a portion of a heart;
tethers extending from the wrapping means, each tether having a magnetic charge; and
instruments each having a magnetic charge, each of the instruments magnetically coupling with a corresponding one of the tethers, each of the at least one instrument further comprising a proximal portion adapted to extend externally from a body cavity such that each magnetically coupled instrument and tether are maneuverable to place the cardiac assist device at a desired position adjacent the heart.

42. The cardiac assist device of claim 41, wherein the wrapping means further comprises a flexible bio-compatible material having a seam at a periphery thereof.

43. The cardiac assist device of claim 42, wherein the wrapping means is comprised of one or more of an elastic, plastic or metal fibers.

44. The cardiac assist device of claim 43, wherein the wrapping means is comprised of a rectangularly shaped material having tethers extending from each corner thereof.

45. The cardiac assist device of claim 43, wherein the wrapping means is comprised of a tri-angularly shaped material having tethers extending from extremities thereof.

46. The cardiac assist device of claim 43, wherein the wrapping means is comprised of a mesh sheet.

47. The cardiac assist device of claim 42, wherein magnets are integrated into the material along portions of the seam for securing the cardiac assist device at a desired position adjacent the heart.

48. The cardiac assist device of claim 47, wherein tethers having similar charges extend from diagonally opposite corners of the rectangularly shaped material.

49. A method for placing a cardiac assist device adjacent a heart within a patient's chest, the chest being defined by a plurality of ribs, each rib being separated by from an adjacent rib by an intercostal space, the method comprising:
providing an access opening within the intercostal space between adjacent ribs;
inserting a cardiac assist device wrap into the chest through the opening, the wrap having at least one tether, each tether haying a magnetic charge;
maneuvering the wrap to a desired position adjacent the heart; and
securing the wrap.

50. The method of claim 49, wherein maneuvering the wrap further comprises:
providing at least one instrument through the opening, each of the at least one instrument having a magnetic charge that magnetically couples with a corresponding one of the at least one tether to position the wrap at the desired position adjacent the heart.

51. The method of claim 49, wherein securing the wrap further comprises: securing the wrap directly to the heart by one of suturing, clipping, stapling or adhering.

52. The method of claim 49, wherein securing the wrap further comprises:
securing anchoring devices to the heart; and
securing the wrap to the anchoring devices.

53. The method of claim 51, wherein the anchoring devices are secured to the heart by one of suturing, clipping, stapling or adhering.

54. The method of claim 52, wherein the anchoring devices provided on a posterior side of the heart are self-anchoring having barbs projecting into the heart.

55. The method of claim 52, wherein the wrap is securing to the anchoring devices by one of suturing, tying, or magnetically attaching thereto.

* * * * *